United States Patent
Yiu

(10) Patent No.: US 10,813,669 B2
(45) Date of Patent: Oct. 27, 2020

(54) MULTI-MOVEMENT COSMETIC DEVICE

(71) Applicant: Soft Lines International, Ltd., Kowloon (HK)

(72) Inventor: Wai Wah Yiu, Kowloon (HK)

(73) Assignee: SOFT LINES INTERNATIONAL, LTD, Hunghom (HK)

( * ) Notice: Subject to any disclaimer, the term of this patent is extended or adjusted under 35 U.S.C. 154(b) by 196 days.

(21) Appl. No.: 15/688,110

(22) Filed: Aug. 28, 2017

(65) Prior Publication Data
US 2018/0055540 A1    Mar. 1, 2018

Related U.S. Application Data

(60) Provisional application No. 62/380,880, filed on Aug. 29, 2016.

(51) Int. Cl.
| | | |
|---|---|---|
| A61B 17/54 | (2006.01) | |
| A45D 44/00 | (2006.01) | |
| A45D 29/05 | (2006.01) | |
| A45D 29/14 | (2006.01) | |
| A61B 17/00 | (2006.01) | |
| A61B 17/32 | (2006.01) | |
| A61B 50/00 | (2016.01) | |

(52) U.S. Cl.
CPC .............. *A61B 17/54* (2013.01); *A45D 29/05* (2013.01); *A45D 29/14* (2013.01); *A45D 44/00* (2013.01); *A45D 2200/1054* (2013.01); *A61B 50/00* (2016.02); *A61B 2017/00398* (2013.01); *A61B 2017/00473* (2013.01); *A61B 2017/00734* (2013.01); *A61B 2017/00761* (2013.01); *A61B 2017/320004* (2013.01)

(58) Field of Classification Search
CPC .......... A61B 17/54; A61B 2017/00752; A61B 2017/00761; A61B 2017/320004; A45D 29/05; A45D 29/14; A46B 13/02; A46B 13/023; A46B 13/026; A46C 17/16; A46C 17/18; A46C 17/24; A46C 17/26; A46C 17/30; A46C 17/32; A46C 17/34; A46C 17/3418; A46C 17/3427; A46C 17/3436; A46C 17/3445; A46C 17/3454; A46C 17/3463; A46C 17/3472; A46C 17/22; A46C 17/221; B24B 23/02
USPC ................................ 451/120, 344, 421, 425
See application file for complete search history.

(56) References Cited

U.S. PATENT DOCUMENTS

| | | | | |
|---|---|---|---|---|
| 8,485,201 B2 * | 7/2013 | Wyatt | ................... | A45D 40/265 132/218 |
| 8,551,117 B2 * | 10/2013 | Yiu | ......................... | A61B 17/54 606/131 |
| 2010/0248598 A1 * | 9/2010 | Matsuda | ................. | B24B 3/546 451/356 |
| 2015/0150352 A1 | 6/2015 | Yiu | | |

(Continued)

*Primary Examiner* — Martin T Ton
(74) *Attorney, Agent, or Firm* — Thomas Coester Intellectual Property

(57) ABSTRACT

A multi-movement cosmetic assembly includes a housing defining an interior; a drive system disposed within the housing; a sleeve received within the housing; and a drive shaft positioned in the sleeve. The drive system is operably coupled to the sleeve and the drive shaft such that actuation of the drive system causes (i) the sleeve to move laterally back and forth to oscillate relative to the housing, and (ii) the drive shaft to rotate relative to the housing.

18 Claims, 15 Drawing Sheets

(56) References Cited

U.S. PATENT DOCUMENTS

2015/0150353 A1\* 6/2015 Yiu ........................ A45D 29/05
132/75.6

\* cited by examiner

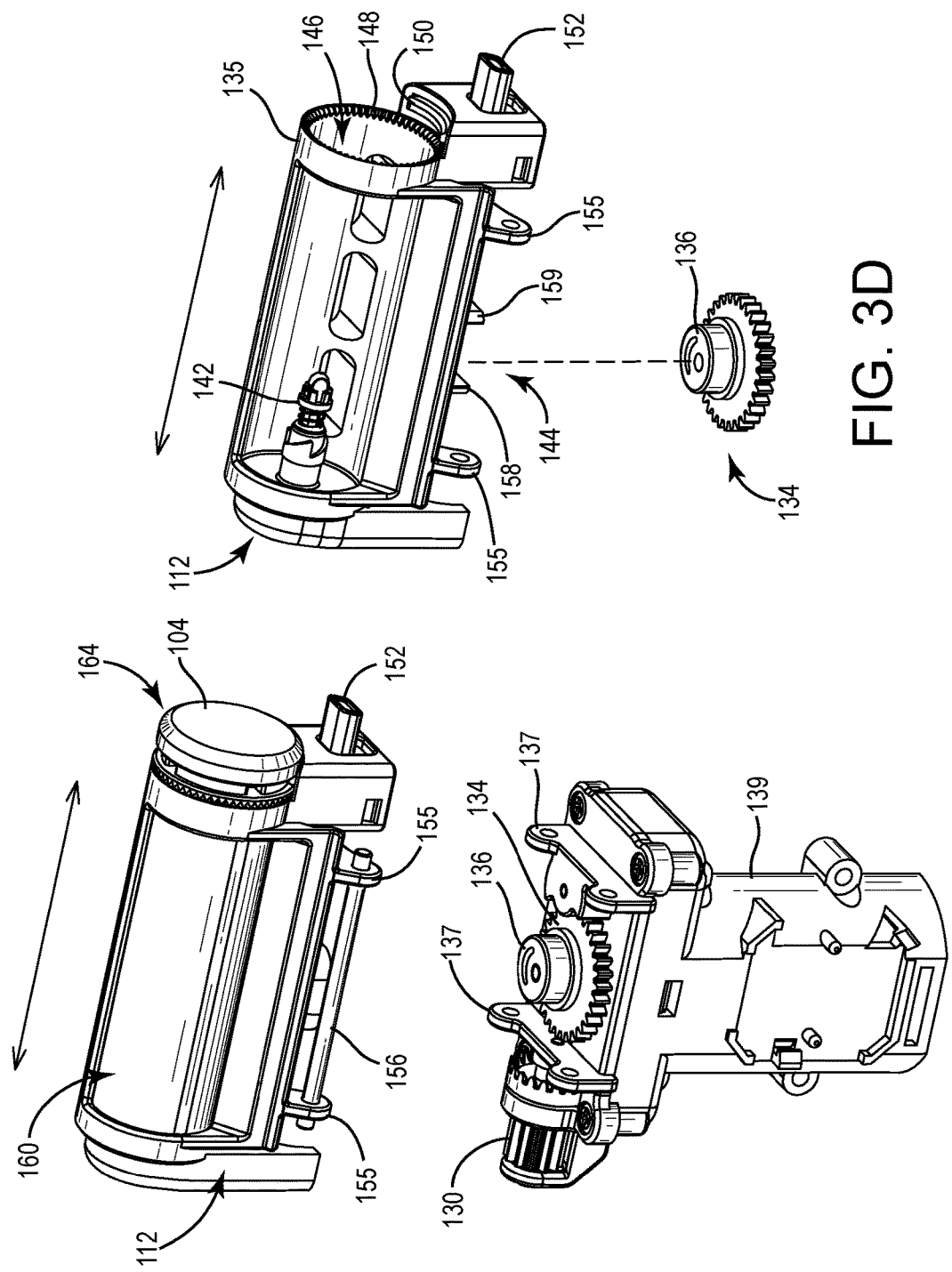

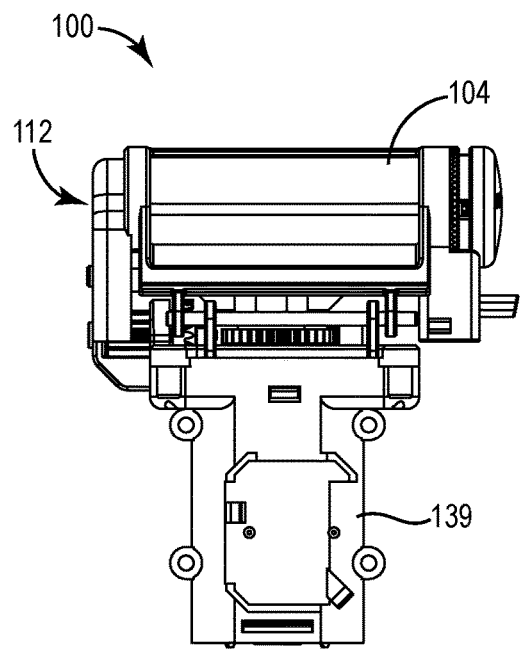
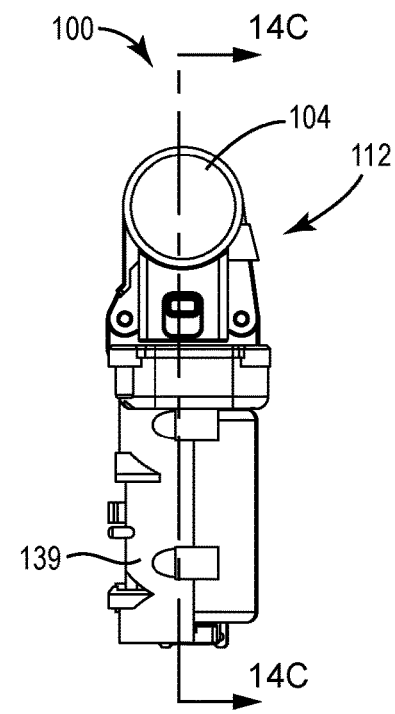
FIG. 14A  FIG. 14B
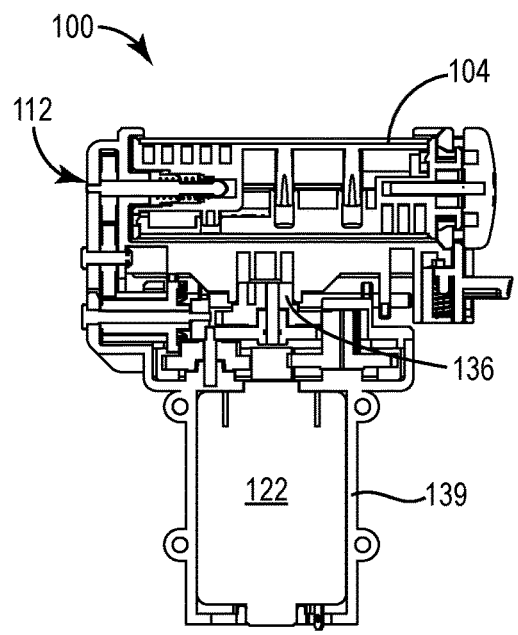
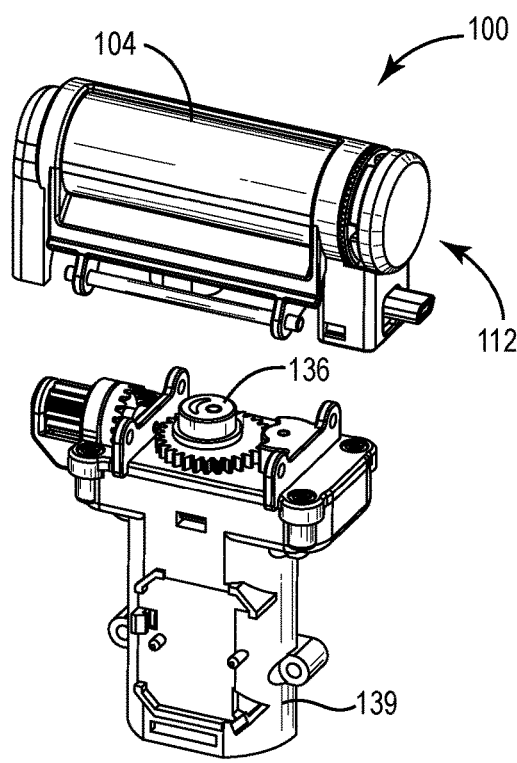
FIG. 14C  FIG. 14D

MULTI-MOVEMENT COSMETIC DEVICE

CROSS-REFERENCE TO RELATED APPLICATIONS

This application claims the benefit of U.S. Provisional Patent Application No. 62/380,880, filed Aug. 29, 2016, which is incorporated by reference herein in its entirety.

BACKGROUND

The present disclosure relates generally to the field of cosmetic devices, and more specifically, to cosmetic devices that provide multi-movement features for users.

Outer layers of skin, hair, nails, etc. may be removed for a variety of reasons and in a variety of ways. A cosmetic device may include cutting blades, abrasive surfaces, or other features to perform such tasks. For example, during a pedicure, dead skin from the bottom of the feet may be removed using a pumice stone. Chemical exfoliant products containing various chemicals such as, salicylic acid, glycolic acid, fruit enzymes, citric acid, or malic acid, can also be used.

Various embodiments disclosed herein are directed to improved multi-movement cosmetic devices and related methods.

SUMMARY

One embodiment relates to a multi-movement cosmetic assembly, including a housing defining an interior; a drive system disposed within the housing; a sleeve received within the housing; and a drive shaft positioned in the sleeve; wherein the drive system is operably coupled to the sleeve and the drive shaft such that actuation of the drive system causes (i) the sleeve to move laterally back and forth to oscillate relative to the housing, and (ii) the drive shaft to rotate relative to the housing.

Another embodiment relates to a multi-movement cosmetic device, including a housing defining an interior; a motor disposed within the housing and including a motor shaft; a drive gear coupled to the motor shaft; a first drive train coupled to the drive gear and including an elongated gear; a second drive train coupled to the drive gear and including a drive wheel; and a sleeve received within the housing and including a drive shaft; a third drive train coupled to the elongated gear and the drive shaft; and a recess configured to receive the drive wheel; wherein actuation of the motor causes (i) the first and third drive trains to rotate the drive shaft; and (ii) the second drive train to rotate the drive wheel within the recess to cause the sleeve to oscillate laterally relative to the housing.

Another embodiment relates to a multi-movement cosmetic assembly, including a device including a housing defining an interior; a drive system disposed within the housing; and a sleeve received within the housing; and an attachment configured to be removably positioned within the sleeve; wherein the drive system is operably coupled to the sleeve and the attachment when the attachment is received within the sleeve such that actuation of the drive system causes (i) the sleeve to move laterally back and forth to oscillate relative to the housing, and (ii) the attachment to rotate within the sleeve and relative to the housing.

BRIEF DESCRIPTION OF THE DRAWINGS

FIG. 3C is an exploded view of a portion of the multi-movement cosmetic device of FIG. 1.

FIG. 3D is an exploded view of a portion of the multi-movement cosmetic device of FIG. 1.

FIG. 14A is a front view of a portion of the multi-movement cosmetic device of FIG. 1 with a sleeve in a left position.

FIG. 14B is a side view of a portion of the multi-movement cosmetic device of FIG. 1 with a sleeve in a left position.

FIG. 14C is a front section view of a portion of the multi-movement cosmetic device of FIG. 1 with a sleeve in a left position.

FIG. 14D is an exploded view of a portion of the multi-movement cosmetic device of FIG. 1 with a sleeve in a left position.

DETAILED DESCRIPTION

Before turning to the Figures, which illustrate the exemplary embodiments in detail, it should be understood that the present application is not limited to the details or methodology set forth in the description or illustrated in the Figures. It should also be understood that the terminology used herein is for the purpose of description and illustration only, and should not be regarded as limiting.

Referring to the Figures generally, various embodiments disclosed herein are directed to cosmetic devices that provide multi-movement features. The cosmetic device may take a variety of forms, and may include one or more attachments to provide various capabilities for users. As such, the cosmetic device may be one or more of an exfoliation device, a shaver, a nose trimmer, a manicure or pedicure device, a facial scrubber, a nail trimmer/filer/polisher, or combinations thereof. In some embodiments, multi-movement refers to both rotational movement about an axis and lateral movement (e.g., a back and forth movement, an oscillating movement) along the axis. For example, a roller assembly may be generally cylindrical in shape and have a longitudinal axis. Various embodiments herein may provide for rotation of the roller assembly about the longitudinal axis, and translation of the roller assembly back and forth along (e.g., parallel to) the longitudinal axis.

Figure 1:
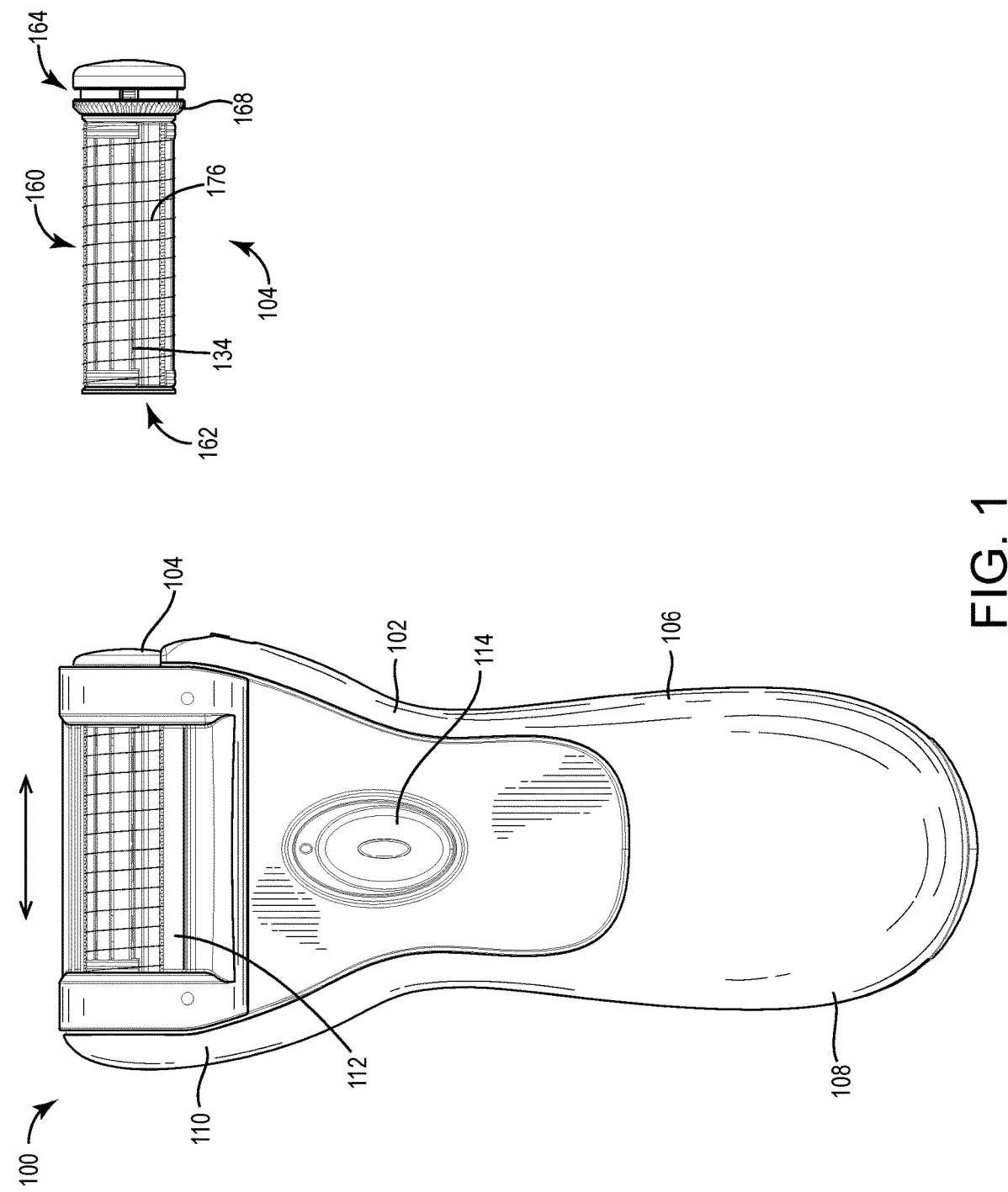
FIG. 1 is a front view of a multi-movement cosmetic device and an attachment, according to an exemplary embodiment.

Referring to FIG. 1, a cosmetic assembly 100 is shown according to an exemplary embodiment and includes a cosmetic device 102 (e.g., a base device or unit) usable with an attachment 104. Device 102 is usable with various different attachments, such that all of the attachments utilize a common interface with the device 102. The device 102 includes a housing 106 that supports and provides mounting for various components within or usable with the device 102. In one embodiment, the housing 106 forms a handle portion 108 and a head portion 110. The handle portion 108 is shaped to provide a comfortable gripping structure and allow a user to hold and manipulate the device 102 in a hand. The handle portion 108 may include various gripping or other features to facilitate grasping of the device 102.

In one embodiment, a power switch 114 is disposed within the housing 106, and is usable to activate and deactivate the device 102 (e.g., by toggling between on and off positions). The power switch 114 is positioned along a front surface of the housing 106 to enable a user to access and move the power switch 114 with a finger while holding the device 102. In one embodiment, the power switch 114 includes a button that must first be depressed to enable movement of the power switch 114.

The head portion 110 of the housing 106 receives a sleeve 112 (e.g., a sliding component, a movable assembly). The sleeve 112 is moveable laterally relative to the housing 106 (e.g., in a left and right direction along the arrow shown in FIG. 1) when the device 102 is activated. The sleeve 112 in turn is configured to receive the attachment 104 (e.g., a removable or replaceable component). FIGS. 1 and 4-9 show various types of attachments and/or accessories that are interchangeably usable with the device 102. In some embodiments, all or a portion of the attachment 104 is received within the sleeve 112. The device 102 is configured such that when activated, the sleeve 112 moves back and forth (e.g., oscillates) relative to the housing 106 (e.g., oscillates left-right), and all or a portion of the attachment 104 rotates within the sleeve 112. As such, the device 102 and attachment 104 provide a multi-movement feature for users, such that the attachment 104 (or portions thereof) will be rotating and translating while being used. As discussed in greater detail below, in some embodiments only a portion of the attachment rotates relative to the sleeve 112, and a remaining portion of the attachment remains stationary.

The various attachments disclosed herein are received within the sleeve 112. The attachment 104 includes a generally cylindrical drum portion 160 to facilitate use during rotation of the attachment 104. A first end of the drum portion 160 includes an aperture or recess 162 configured to receive a drive shaft 142 of the device 102 (e.g., such that the rotation of the drive shaft 142 causes a corresponding rotation of the attachment 104 or portions thereof). A second end of the drum portion 160 is coupled to a hub 164, where the hub 164 includes a plurality of splines, or projections 168, extending circumferentially about the hub 164.

Figure 2:
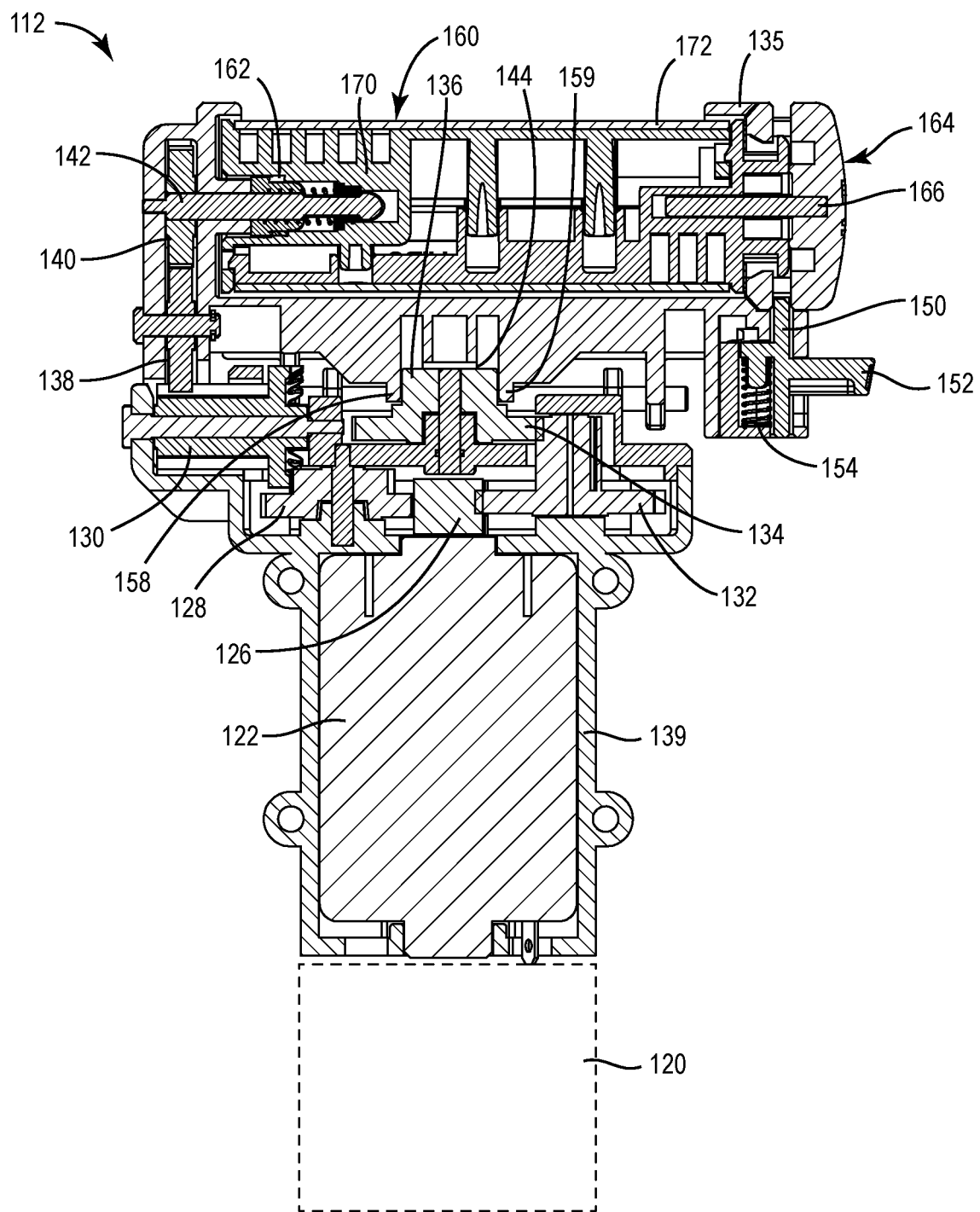
FIG. 2 is a front section view of a portion of the multi-movement cosmetic device of FIG. 1.

Referring to FIG. 2, in some embodiments, the device 102 includes a motor 122 configured to move the sleeve 112 and attachment 104. A power source 120 (e.g., a battery) provides power to the motor 122 (e.g., through the power switch 114), and a drive mechanism (e.g., a gear train, drive train, etc.) transmits power from the motor 122 to the sleeve 112 and the attachment 104. In one embodiment, the device 102 may include any of the features shown in the cosmetic device disclosed in U.S. Pat. No. 8,551,117, which is incorporated herein by reference in its entirety, including those features relating to the attachment 104 and the interface of the attachment 104 and the device 102.

Figure 3A:
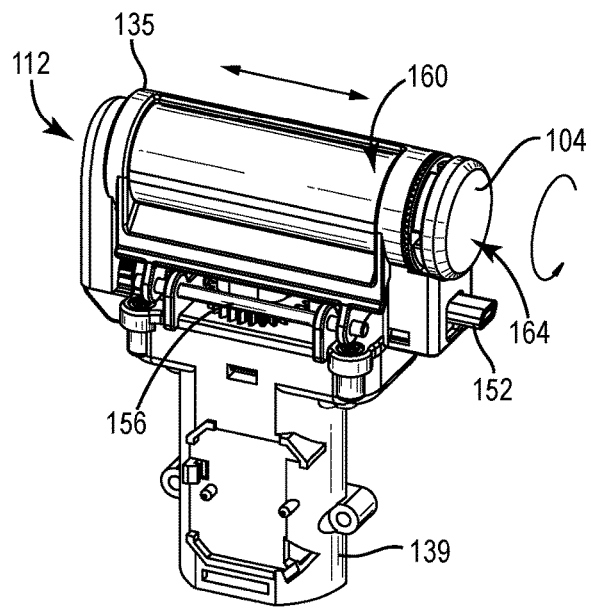
FIG. 3A is a perspective view of a portion of the multi-movement cosmetic device of FIG. 1.
Figure 3B:
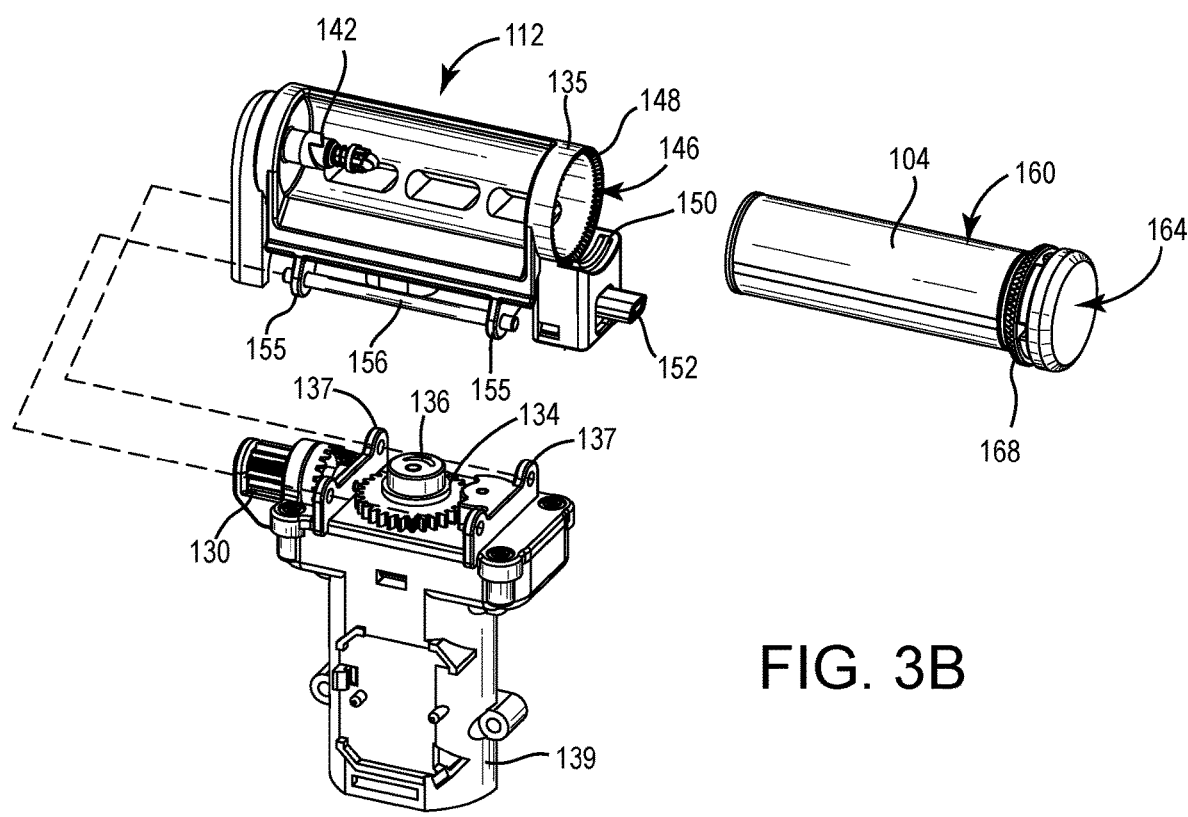
FIG. 3B is an exploded view of a portion of the multi-movement cosmetic device of FIG. 1.

Referring to FIGS. 2-3D, the sleeve 112 and the drive mechanism for the device 102 are shown in greater detail according to one embodiment. The motor 122 (e.g., electric motor) is received within the housing 106. In one embodiment, the motor 122 includes a motor shaft. The motor shaft is coupled to a first gear 126 (e.g., a drive gear). A second gear 128 engages a first side of the first gear 126. In one embodiment, the second gear 128 includes a first portion engaging the first gear 126 and a second portion positioned above the first portion. A third gear 130 engages the second gear 128. In one embodiment, the third gear 130 includes a first portion engaging the second portion of the second gear 128 at a right angle, and a second portion. In some embodiments, the second portion of the third gear 130 is elongated to accommodate the oscillation of the sleeve 112. In one embodiment, the first, second, and third gears 126, 128, 130 form a first drive train or gear train.

A fourth gear 138 is coupled to the elongated portion of the third gear 130. The elongated portion of the third gear 130 is wider than (i.e., elongated relative to) the fourth gear 138 such that the fourth gear 138 can translate relative to the third gear 130 while continuing to engage the third gear 130 (e.g., while the sleeve 112 oscillates). A fifth gear 140 engages the fourth gear 138 and is coupled to the drive shaft 142. The drive shaft 142 is configured to receive or be received by the attachment 104 such that rotation of the drive shaft 142 causes a corresponding rotation of all or a portion of the attachment 104. In some embodiments, the fourth and fifth gears 138, 140 form a third drive train or gear train as part of the sleeve 112.

A sixth gear 132 engages the first gear 126 (e.g., at an opposite side of the second gear 128). In one embodiment, the sixth gear 132 includes a first portion engaging the first gear 126 and a second portion positioned above the first portion. A seventh gear 134 engages the sixth gear 132. In one embodiment, the seventh gear 134 includes a first portion engaging the second portion of the sixth gear 132 and a second portion. In some embodiments, the second portion of the seventh gear 134 forms a drive wheel 136. In one embodiment, the drive wheel 136 is mounted eccentrically relative to the center of the first portion of the seventh gear 134. For example, the drive wheel 136 may include a cylindrical portion having a longitudinal axis that is offset from the axis of the first portion of the seventh gear 134. The drive wheel 136 is in one embodiment cylindrical in shape and includes a substantially smooth cylindrical sidewall configured to engage an inner surface of a recess 144 of the sleeve 112. The first, sixth, and seventh gears 126, 132, 134 form a second drive train, or gear train.

In operation, actuation of the motor 122 causes rotation of the motor shaft and in turn, the first gear 126, or drive gear. Rotation of the first gear 126 causes a corresponding rotation of the elongated portion of the third gear 130 (e.g., via the first drive train) and a corresponding rotation of the drive wheel 136 (e.g., via the second drive train). Rotation of the third gear 130 causes a corresponding rotation of the fourth gear 138. Rotation of the fourth gear 138 causes a corresponding rotation of the drive shaft 142 (e.g., via the third drive train). Rotation of the drive wheel 136 within the recess 144 of the sleeve 112 causes a corresponding oscillation of the sleeve 112 (e.g., due to rotation of the eccentrically mounted drive wheel 136 within the recess 144 of the sleeve 112). Accordingly, the fourth gear 138 oscillates along a length of the elongated portion of third gear 130 such that the third gear 130 and the fourth gear 138 engage each other in both a rotational and a translational manner.

In one embodiment, the sleeve 112 includes one or more guide members 156 to facilitate smooth oscillation of the sleeve 112. For example, as shown in FIGS. 3A-3D, the sleeve 112 may include one or more elongated guide members 156 shown as rods (e.g., one on each side of the sleeve 112). One or more spaced apart end members 155 may couple the guide members 156 to a remainder of the sleeve 112. The guide members 156 may be received in supports 137 provided on an internal housing 139 in which the motor 122 is received. The supports 137 and end members 155 are in one embodiment positioned to limit the degree of lateral movement, or oscillation, of the sleeve 112. In other embodiments, the degree of lateral movement, or oscillation, of the sleeve 112 is limited by the interaction between the drive wheel 136 and the recess 144 of the sleeve 112.

The sleeve 112 includes a sleeve housing 135 configured to receive the attachment 104. The sleeve housing 135 includes a plurality of circumferentially positioned projections 148, or splines, configured to engage corresponding projections 168 on the attachment 104 and rotationally fix a portion of the attachment 104 relative to the sleeve housing 135. In some embodiments, the sleeve 112 includes a support bracket 150 configured to engage a hub portion 164 of the attachment 104 (e.g., an annular groove). The support bracket 150 may have a curve corresponding to an outer curve portion of the attachment 104. In some embodiments, the support bracket 150 is biased toward the hub 164 by a spring 154 or other device, and includes a lever 152 that a user may depress to move the support bracket 150 out of engagement with the hub 164.

The recess 144 in the sleeve 112 is at least partially defined by two opposing sidewalls 158, 159. In one embodiment, the sidewalls 158, 159 are spaced apart a distance just wide enough to receive the drive wheel 136. As such, as the drive wheel 136 rotates, the eccentric mounting causes the drive wheel 136 to engage the sidewalls 158, 159 of the recess 144 and move the sleeve 112 in an oscillating fashion.

In one embodiment, the attachment 104 includes a drum portion 160 received by the sleeve 112 and a hub portion 164. The drum portion 160 includes an inner portion 170 and an outer portion 172. The inner portion 170 includes a recess 162 configured to receive the drive shaft 142 and rotate with the drive shaft 142. The hub 164 includes a plurality of circumferentially positioned projections 148, or splines, configured to engage the corresponding projections 168 on the sleeve housing 135. In some embodiments the outer portion 172 of the drum portion 160 rotates with the inner portion 170 of the drum portion 160, and in other embodiments, the outer portion 172 of the drum portion 160 remains stationary with the hub 164. The inner portion 170 in some embodiments further includes a secondary shaft 166. The secondary shaft 166 extends from the inner portion 170. In some embodiments, the secondary shaft 166 extends beyond the hub 164 to receive additional components. In the embodiment shown in FIG. 2, the secondary shaft 166 is fixed to one of the hub 164 and the drum portion 160 and rotates relative to the other of the hub 164 and the drum portion 160 to permit relative rotation between the drum portion 160 and the hub 164.

Referring now to FIGS. 1 and 4-7, attachments are shown according to various alternative embodiments. As discussed in greater detail below, the attachments are configured to be received within the sleeve 112. As such, the attachments oscillate laterally with the sleeve 112 relative to the housing 106. A portion of the attachments rotate relative to the sleeve 112, and therefore, the housing 106. Each attachment generally includes a working portion, or member (e.g., the portion of the attachment that is configured to abrade, trim, shine, polish, trim, etc., such as an abrasive member, a trimming member, etc.). The working portion may be provided as part of the drum portion (e.g., be confined between the lateral sides of the sleeve housing 135), or alternatively, may be provided as an additional member extending out from the hub of the attachment (e.g., as a separate working portion or member). Each of the attachments includes a hub having projections extending therefrom that interact with the circumferentially positioned projections 148 to prevent rotation of the hub relative to the sleeve 112. Additionally, the hubs each define an annular groove configured to receive the support bracket 150.

Referring back to FIG. 1, the device 102 is shown with the attachment 104 as a shaving attachment. In one embodiment, the attachment 104 is or includes a shaving accessory in the form of a shaving roller assembly. The roller assembly includes a number of parallel blades 174 extending parallel to the longitudinal axis of the roller assembly and a protective member 176 (e.g., wire) wound circumferentially around the blades 174 to protect a user's skin. As such, the working portion (e.g., the blades 174) of the attachment 104 is provided on the drum portion 160, which rotates with the drive shaft 142 while the hub 164 portion remains stationary. The attachment 104, and therefore, the working portion, oscillates with the sleeve 112 during operation of the device 102. In alternative embodiments, the working portion may be provided as an abrasive and/or compressible surface.

Figure 4:
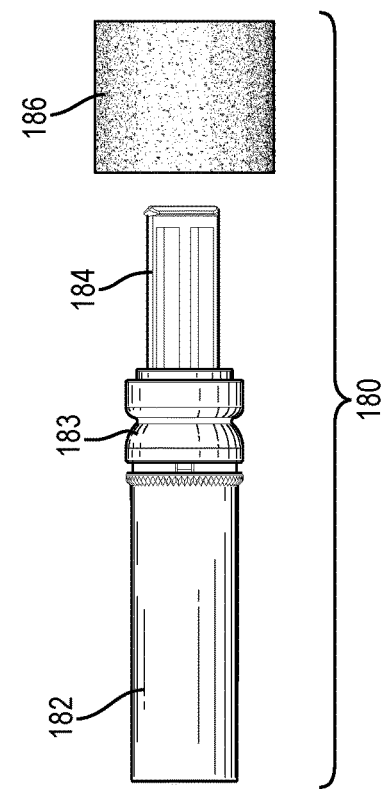
FIG. 4 is a front view of the multi-movement cosmetic device of FIG. 1 and another attachment, according to an exemplary embodiment.
Figure 4:
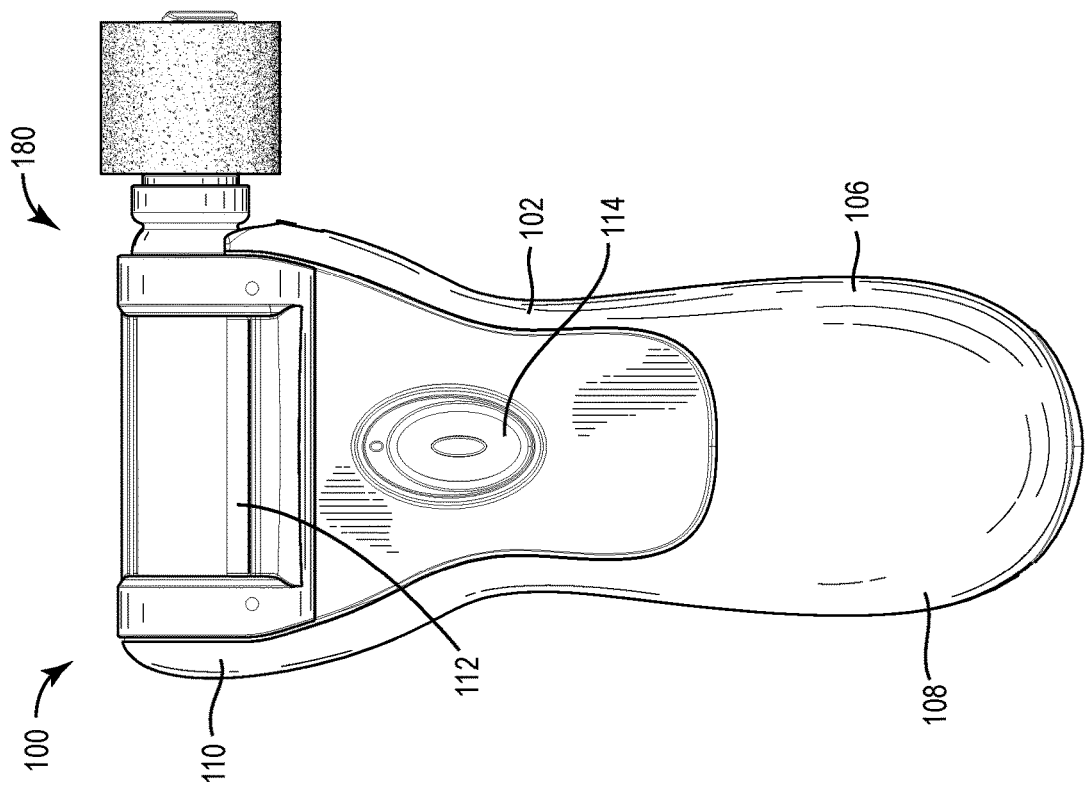

As shown in FIG. 4, the device 102 is shown with another attachment 180. The attachment 180 in FIG. 4 includes an abrasive roller 186 (e.g., a manicure attachment). For example, a drum portion 182 and a hub 183 of the attachment 180 may remain stationary while the roller 186 rotates with the drive shaft 142. In one embodiment, the attachment 180 includes an accessory shaft 184 that is operatively coupled to the drive shaft 142, such that the roller 186 is received on the shaft 184. The roller 186 may include an abrasive outer surface and a compressible core portion defining an aperture to receive the shaft 184. Alternative rollers may include any disclosed in U.S. Publication No. 2015-0150352, which is incorporated herein by reference in its entirety.

Figure 5:
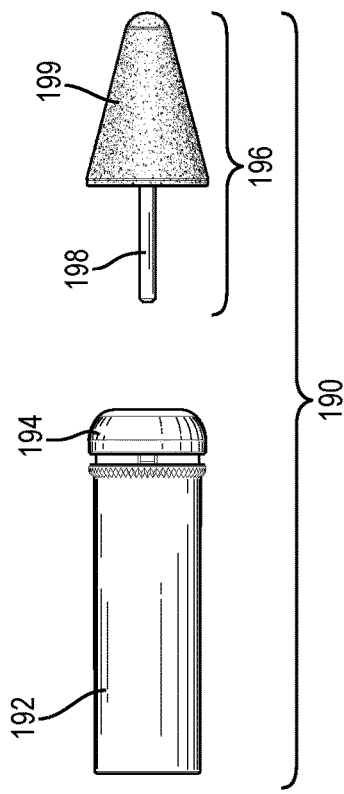
FIG. 5 is a front view of the multi-movement cosmetic device of FIG. 1 and another attachment, according to an exemplary embodiment.
Figure 5:
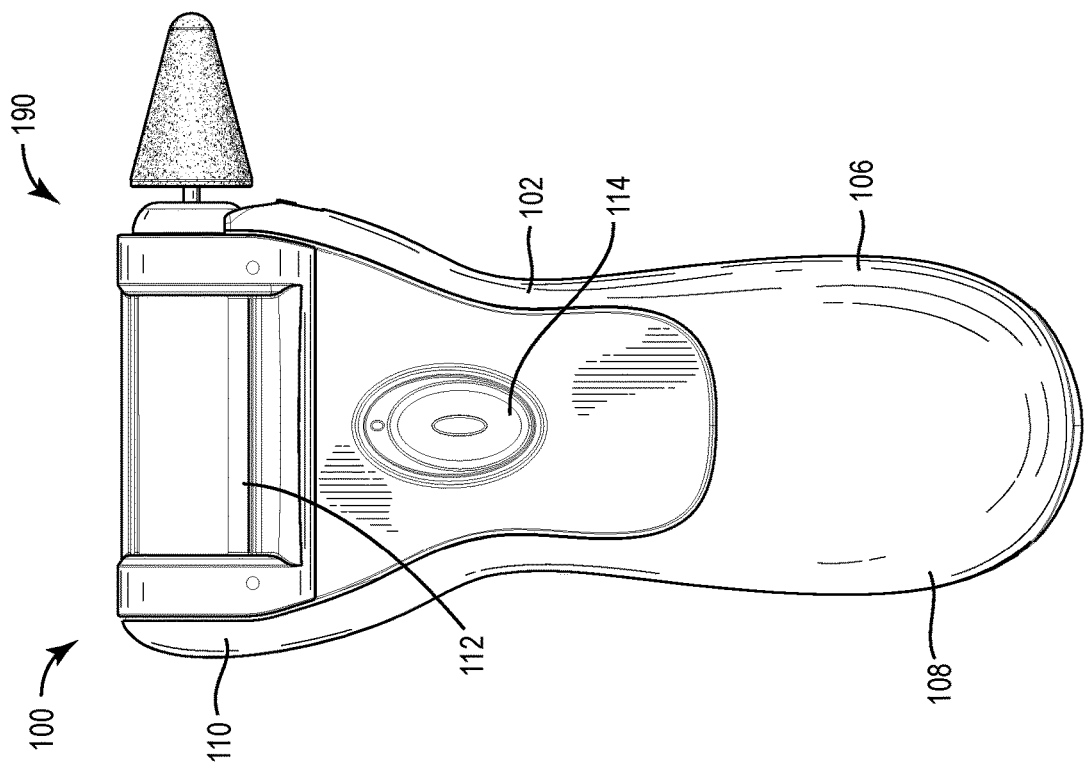
Figure 6:
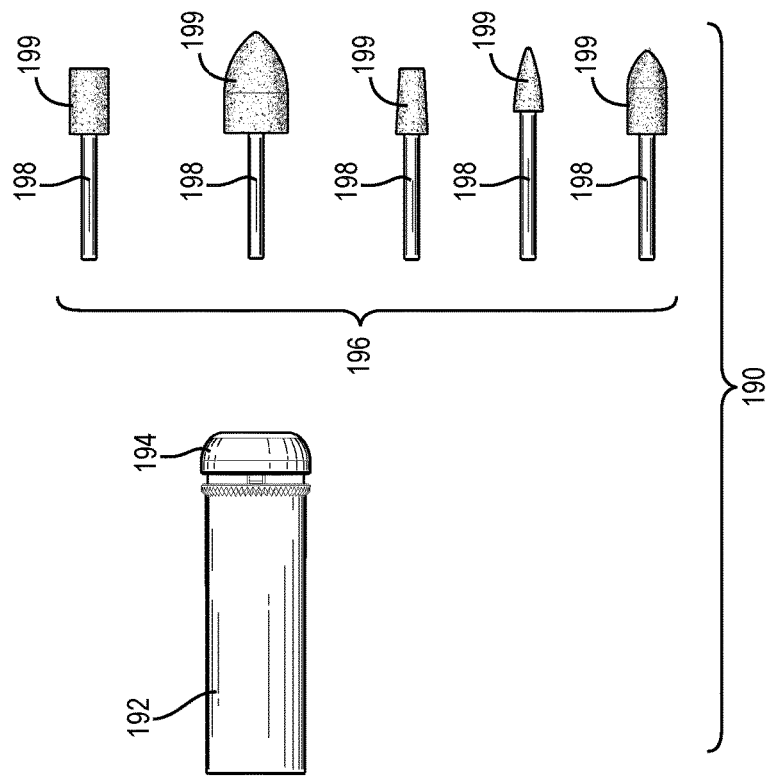
FIG. 6 is a front view of the multi-movement cosmetic device of FIG. 1 and another attachment, according to an exemplary embodiment.
Figure 6:
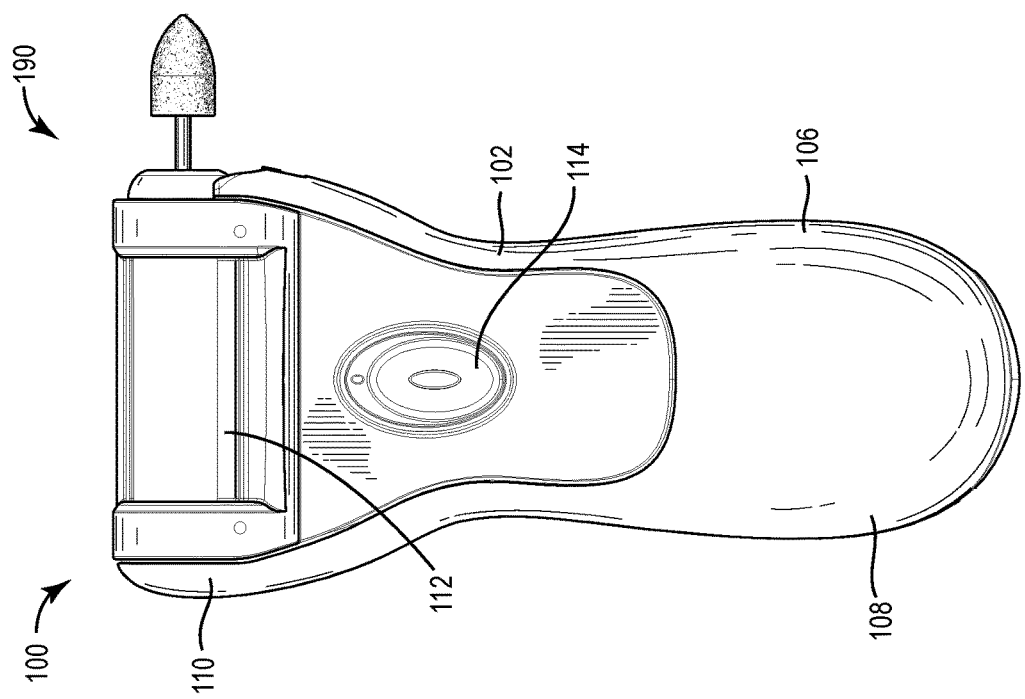

As shown in FIG. 5, the device 102 is shown with another attachment 190. The attachment 190 in FIG. 5 includes a drum portion 192, a hub 194, and an accessory 196. The accessory 196 in one embodiment includes a shaft 198 and an abrasive member 199. The shaft 198 is received by the hub 194 of the attachment 190 and the abrasive member 199 is rotationally fixed relative to the shaft 198. The abrasive member 199 may be compressible, or alternatively, formed of a hard, stone or stone-like material. The abrasive member 199 may be tapered and have a rounded tip portion. As shown in FIG. 6, the abrasive member 199 may take a variety of forms for various applications. In some embodiments, the accessory 196 is removable (e.g., without the use of tools) to facilitate replacement.

Figure 7:
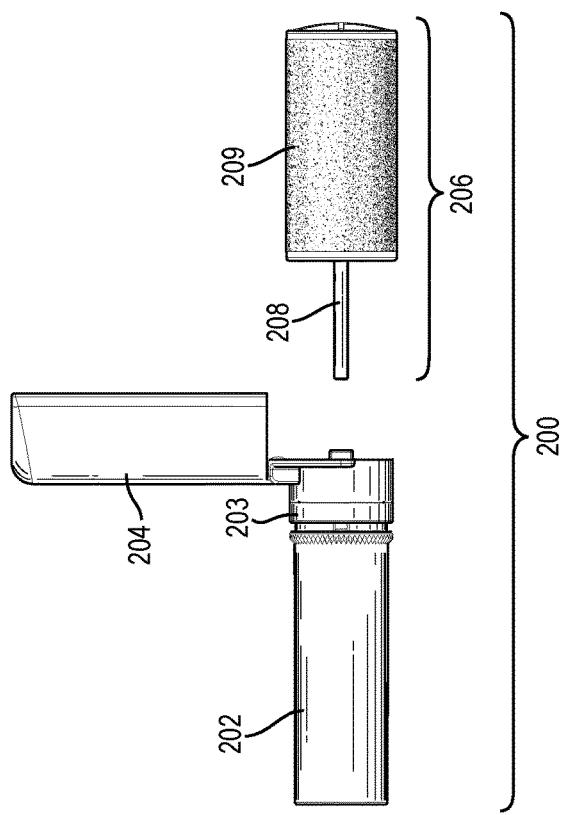
FIG. 7 is a front view of the multi-movement cosmetic device of FIG. 1 and another attachment, according to an exemplary embodiment.
Figure 7:
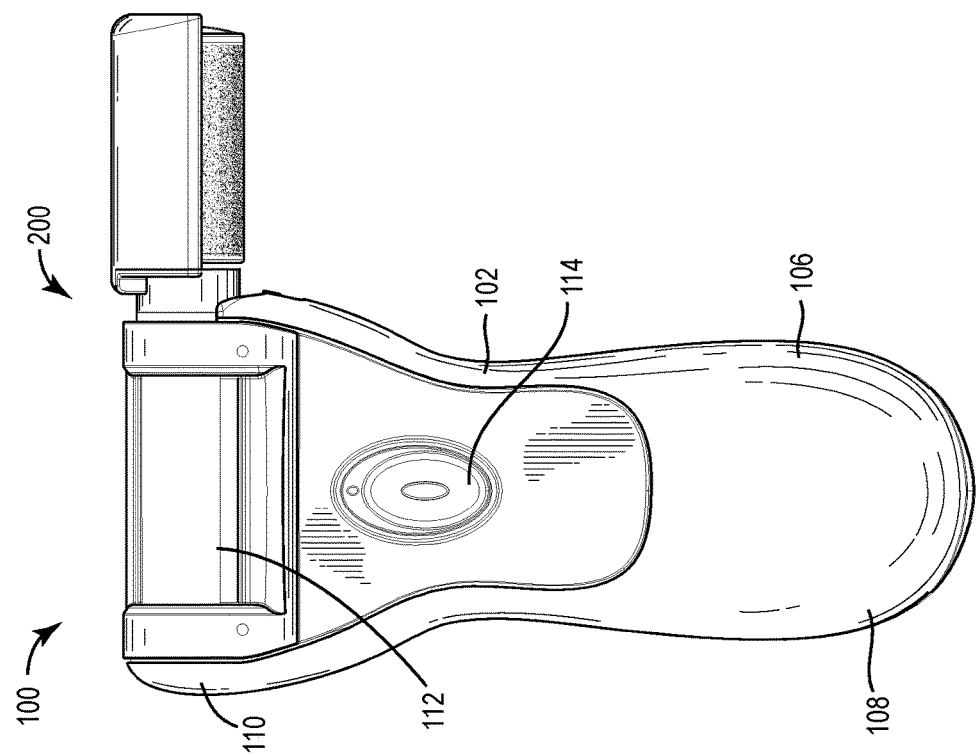

As shown in FIG. 7, the device 102 is shown with another attachment 200 according to an alternative embodiment. The attachment 200 in FIG. 7 includes a drum portion 202, a hub 203, a cover 204, and an accessory 206. The accessory 206 includes a shaft 208 and an abrasive member 209. The attachment 200 is usable in a variety of ways, including as a body (e.g., skin, etc.) scrub attachment. The abrasive member 209 is generally cylindrical in shape, and may provide a compressible or substantially non-compressible abrasive surface. The cover 204 is configured to rotate between a first position adjacent the accessory 206 and a second position rotated away from the accessory 206. The cover 204 is rotatably coupled to the hub 203, and does not rotate with the abrasive member 209. In one embodiment, the drum portion 202 of the attachment 200 remains stationary relative to the hub 203.

Figure 8:
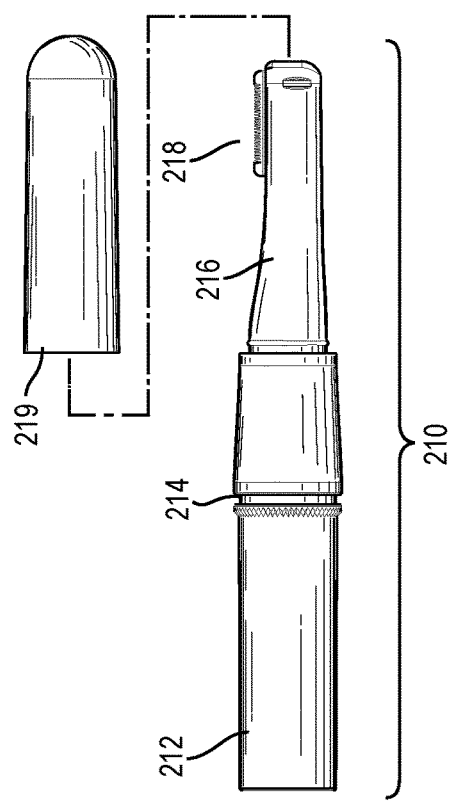
FIG. 8 is a front view of the multi-movement cosmetic device of FIG. 1 and another attachment, according to an exemplary embodiment.
Figure 8:
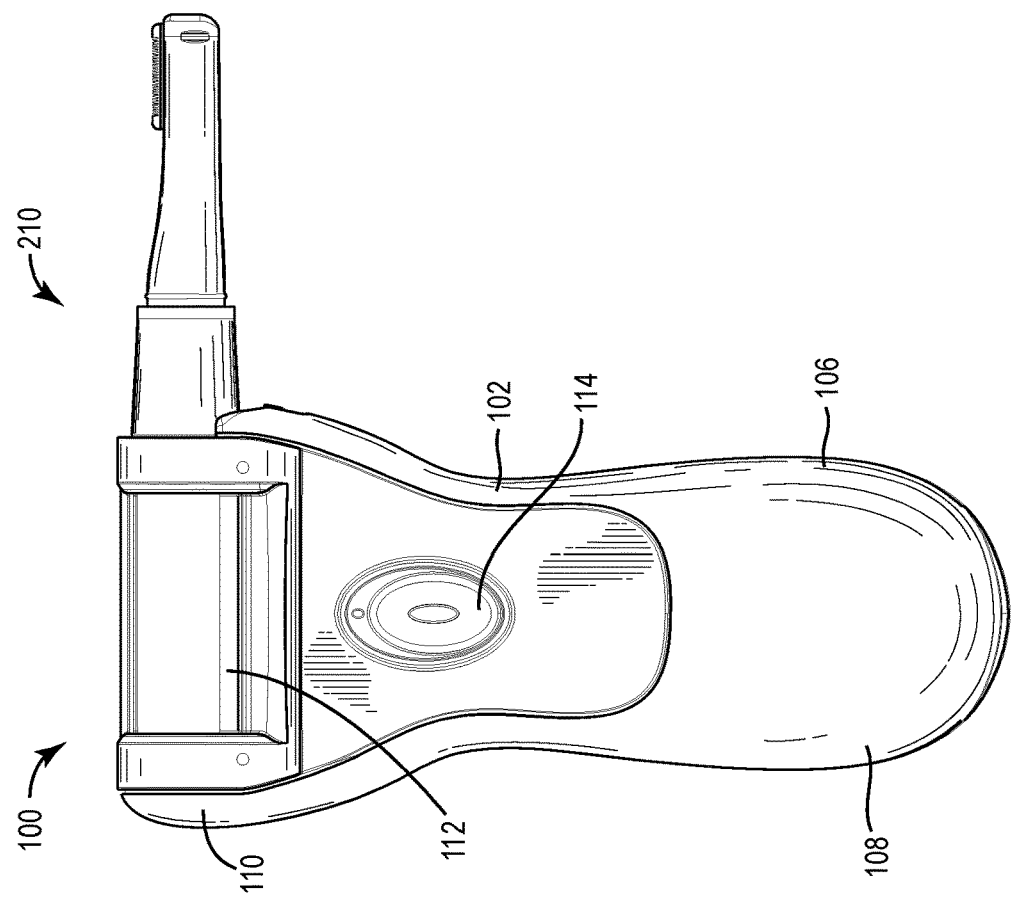

As shown in FIG. 8, the device 102 is shown with another attachment 210 according to an alternative embodiment. The attachment 210 provides a facial hair trimmer or shaver. The attachment 210 in FIG. 8 includes a drum portion 212, a hub 214, an extension portion 216, a trimmer portion 218, and a cover 219. In one embodiment, the extension portion 216 oscillates with the sleeve 112 but remains rotationally fixed relative to the hub 214 and the sleeve 112. The trimmer portion 218 includes blades that are oscillated based on the rotation of the drive shaft 142. The cover 219 is removable to cover the trimmer portion 218 when not in use.

Figure 9:
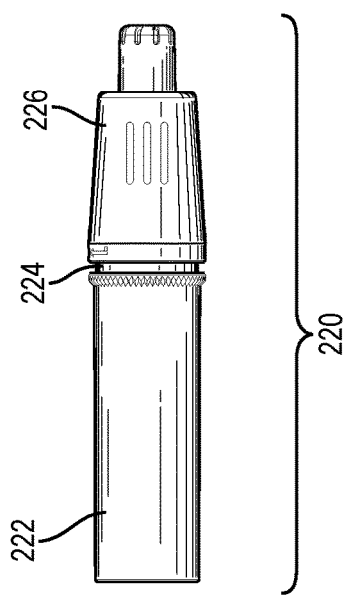
FIG. 9 is a front view of the multi-movement cosmetic device of FIG. 1 and another attachment, according to an exemplary embodiment.
Figure 9:
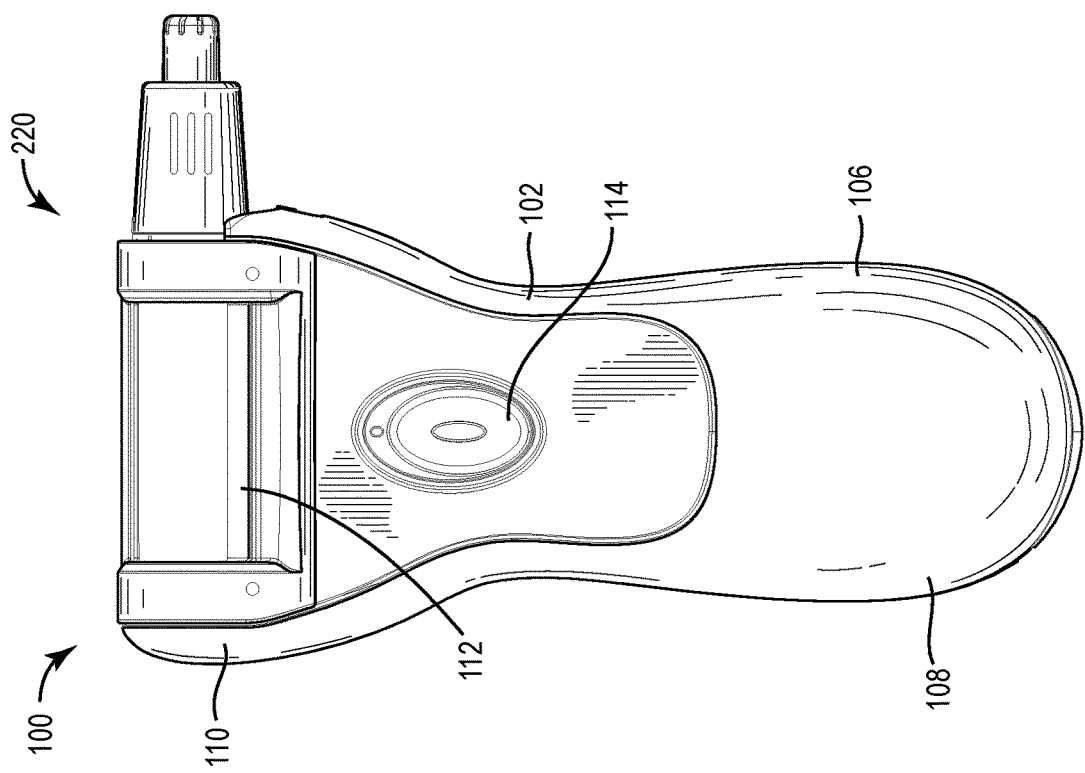

As shown in FIG. 9, the device 102 is shown with another attachment 220 according to an alternative embodiment. The attachment 220 provides a nose and/or ear hair trimmer. The attachment 220 includes a drum portion 222, a hub 224, and an extension portion 226. In one embodiment, the extension portion 226 includes a first relatively larger diameter portion, and a second, relatively smaller diameter portion. A blade or blades coupled to the drive shaft 142 is provided within the smaller portion and is configured to trim nose hair, ear hair, etc. The extension portion 226 remains rotationally fixed while the blade(s) rotate within the extension portion 226 and trim hair through slots, or apertures, provided in the extension portion 226.

Figure 10C:
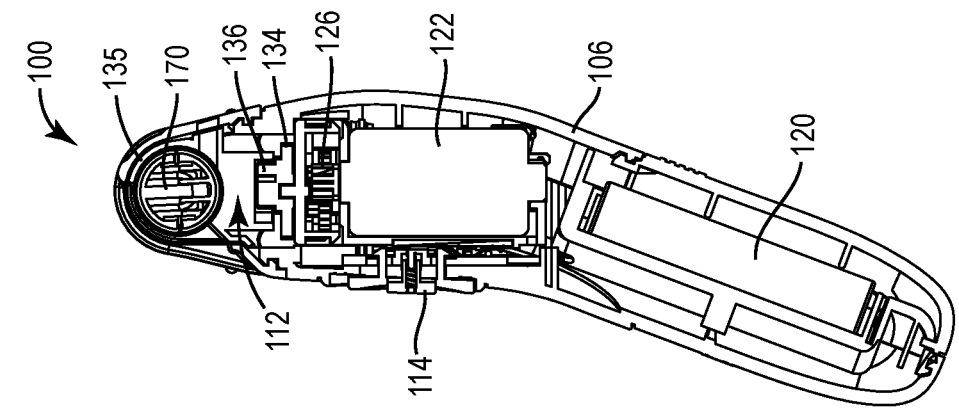
FIG. 10C is a side section view of the multi-movement cosmetic device of FIG. 1.
Figure 10B:
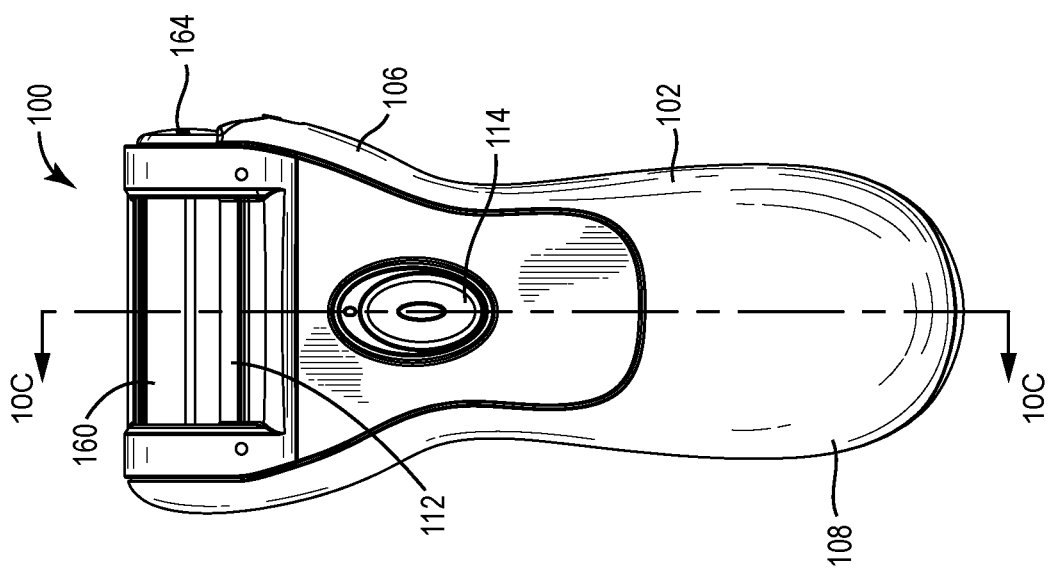
FIG. 10B is a front view of the multi-movement cosmetic device of FIG. 1.
Figure 10A:
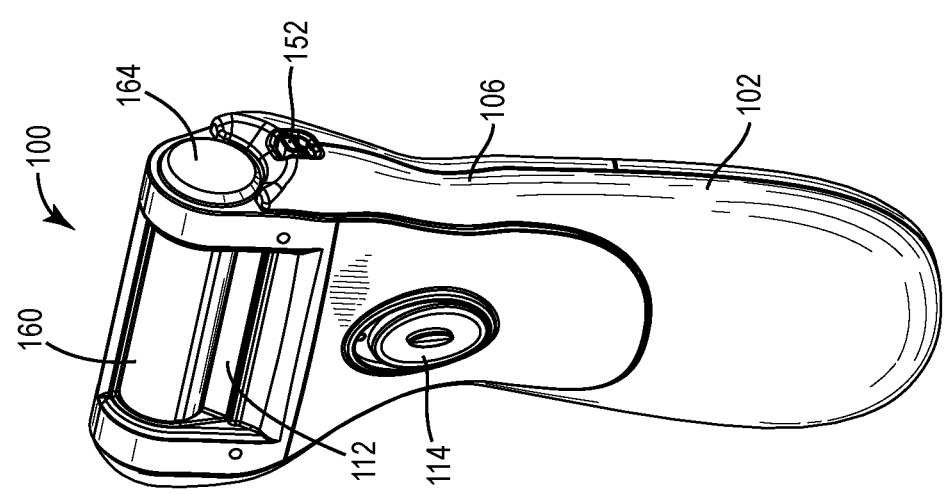
FIG. 10A is a perspective view of the multi-movement cosmetic device of FIG. 1.
Figure 11:
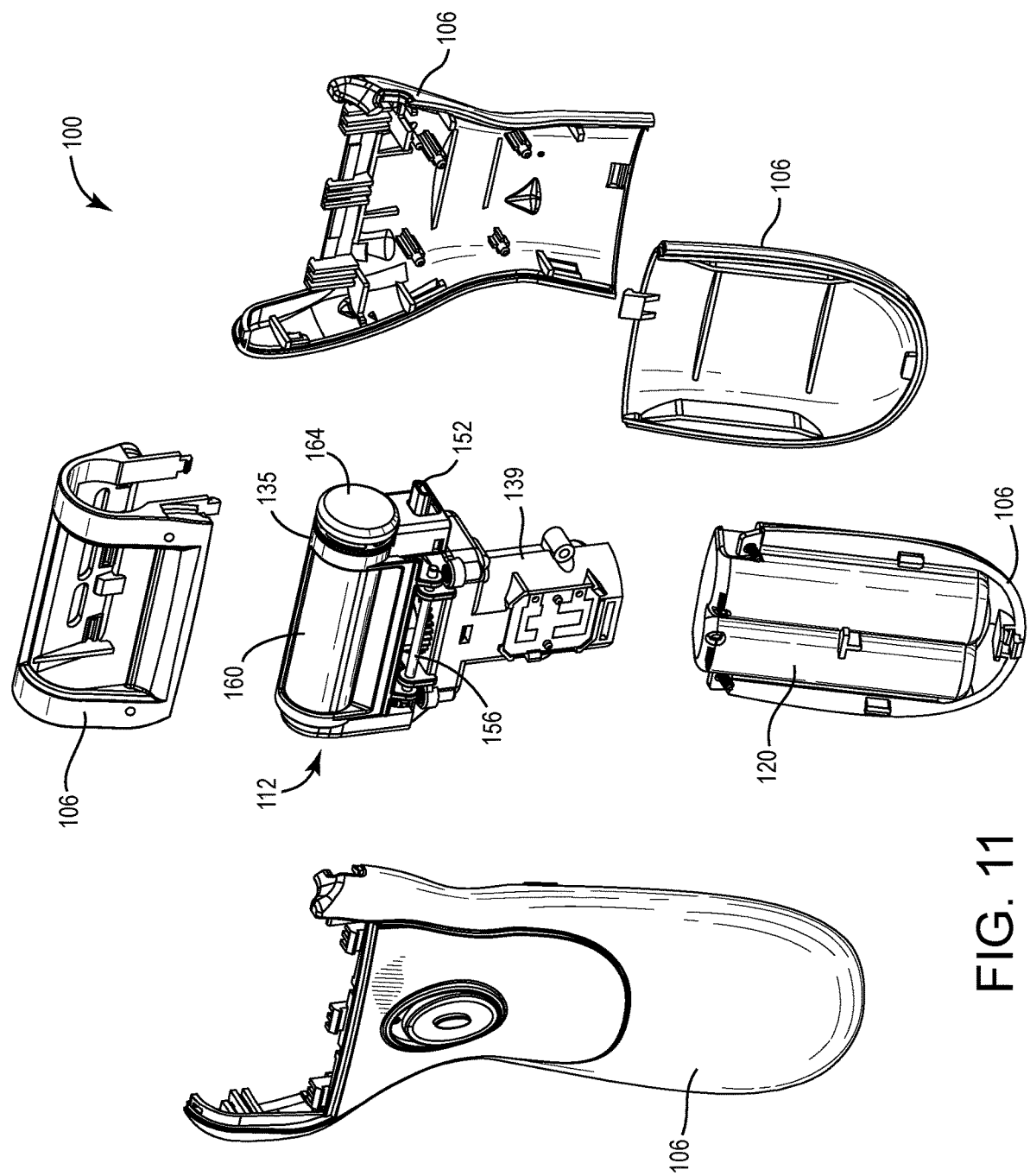
FIG. 11 is an exploded view of the multi-movement cosmetic device of FIG. 1.
Figure 12A:
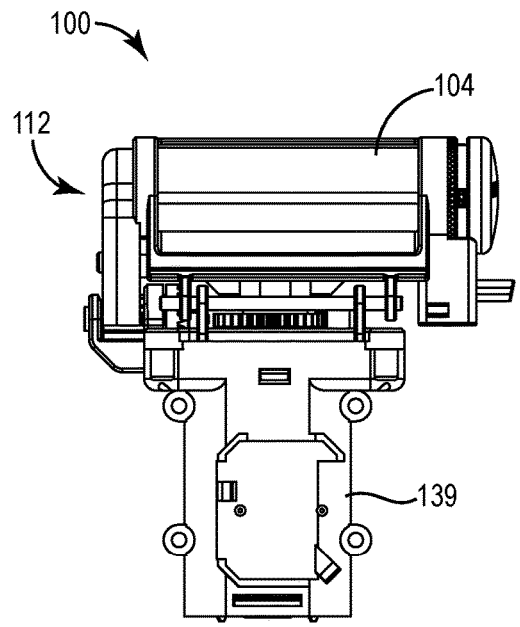
FIG. 12A is a front view of a portion of the multi-movement cosmetic device of FIG. 1 with a sleeve in a right position.
Figure 12B:
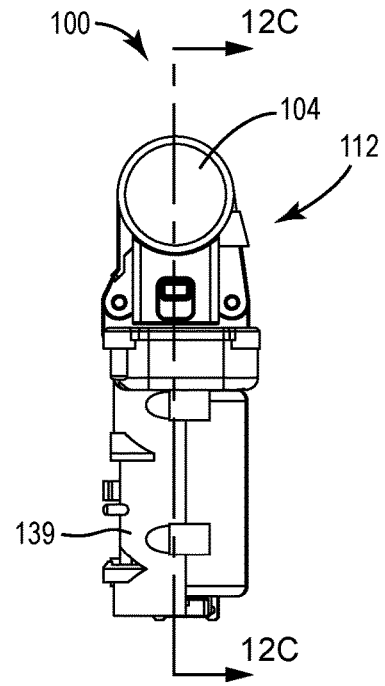
FIG. 12B is a side view of a portion of the multi-movement cosmetic device of FIG. 1 with a sleeve in a right position.
Figure 12C:
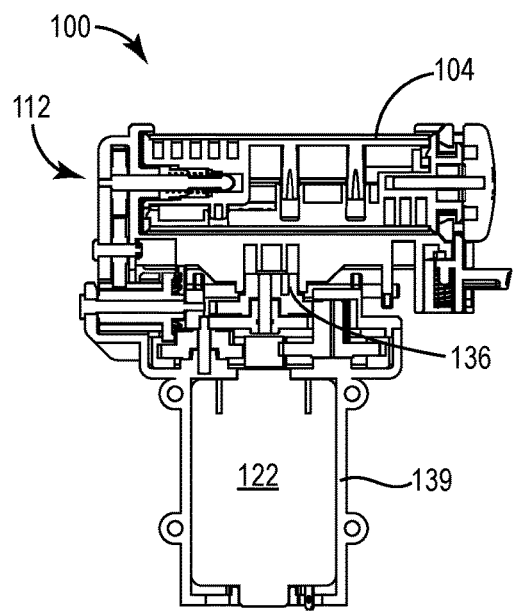
FIG. 12C is a front section view of a portion of the multi-movement cosmetic device of FIG. 1 with a sleeve in a right position.
Figure 12D:
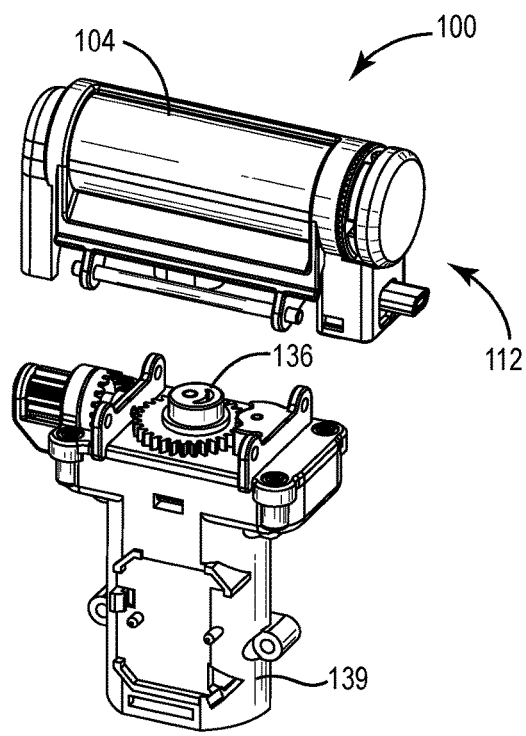
FIG. 12D is an exploded view of a portion of the multi-movement cosmetic device of FIG. 1 with a sleeve in a right position.
Figure 13A:
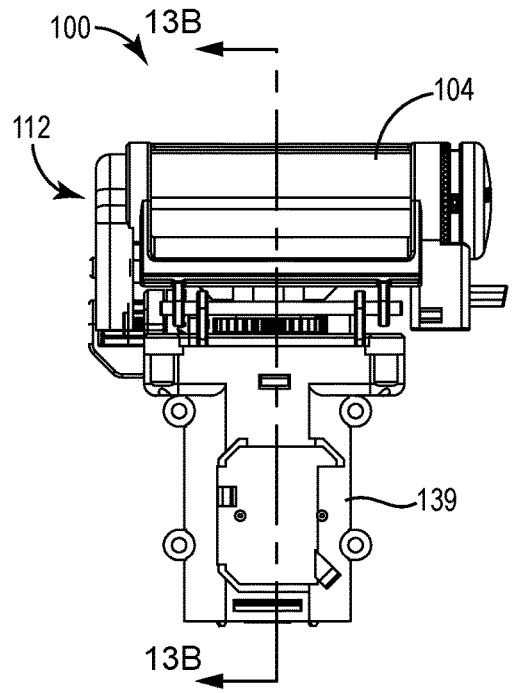
FIG. 13A is a front view of a portion of the multi-movement cosmetic device of FIG. 1 with a sleeve in a middle position.
Figure 13B:
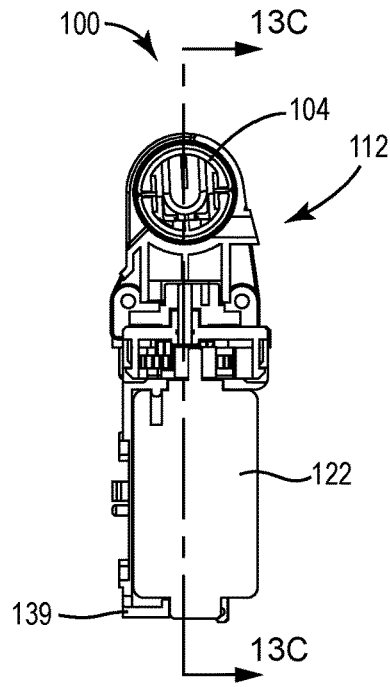
FIG. 13B is a side section view of a portion of the multi-movement cosmetic device of FIG. 1 with a sleeve in a middle position.
Figure 13C:
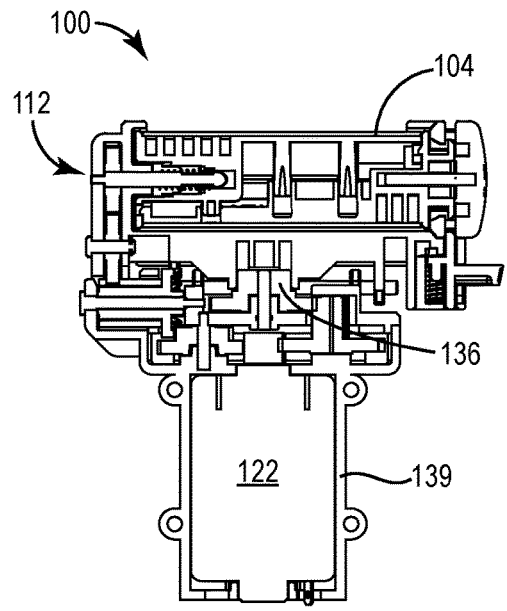
FIG. 13C is a front section view of a portion of the multi-movement cosmetic device of FIG. 1 with a sleeve in a middle position.
Figure 13D:
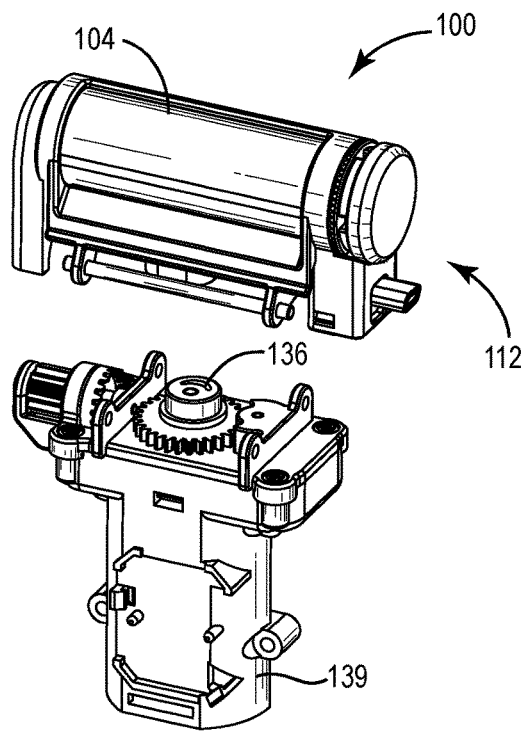
FIG. 13D is an exploded view of a portion of the multi-movement cosmetic device of FIG. 1 with a sleeve in a middle position.

FIGS. 10A-14D illustrate additional details regarding device 102 and attachment 104. FIGS. 10A-11 illustrate the positioning of the sleeve 112 and the housing 139 within housing 106. The housing 106 includes multiple sections that couple to one another (e.g., with snaps, with screws, with clips, with adhesive, etc.). When assembled, the housing 106 surrounds all but a portion of the sleeve 112, the drum portion 160, and the hub 164. In some embodiments, the housing 106 is completely or partially sealed such that the cosmetic assembly 100 is completely or partially water resistant. FIGS. 12A-14D illustrate the sleeve 112 in various positions, for example, a right position (FIGS. 12A-12D), a middle position (FIGS. 13A-13D), and a left position (FIGS. 14A-14D).

Further modifications and alternative embodiments of various aspects of the invention will be apparent to those skilled in the art in view of this description. Accordingly, this description is to be construed as illustrative only. The construction and arrangements shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.) without materially departing from the novel teachings and advantages of the subject matter described herein. Some elements shown as integrally formed may be constructed of multiple parts or elements, the position of elements may be reversed or otherwise varied, and the nature or number of discrete elements or positions may be altered or varied. The order or sequence of any process, logical algorithm, or method steps may be varied or re-sequenced according to alternative embodiments. Other substitutions, modifications, changes and omissions may also be made in the design, operating conditions and arrangement of the various exemplary embodiments without departing from the scope of the present invention.

What is claimed is:

1. A multi-movement cosmetic assembly, comprising:
a housing defining an interior;
a drive system disposed within the housing;
a sleeve received within the housing; and
a drive shaft positioned in the sleeve;
wherein the drive system is operably coupled to the sleeve and the drive shaft such that actuation of the drive system causes (i) the sleeve to move laterally back and forth to oscillate relative to the housing, and (ii) the drive shaft to rotate relative to the housing, and
wherein the drive system includes:
a motor;
a first gear train operably coupled to the motor;
a second gear train operably coupled to the motor and configured to oscillate the sleeve; and
a third gear train configured to transmit power from the first gear train to the drive shaft.

2. The assembly of claim 1, wherein at least one gear of the first gear train and at least one gear of the third gear train engage each other during operation of the assembly in both a rotational and translational manner.

3. The assembly of claim 2, wherein the at least one gear of the first gear train is elongated relative to the at least one gear of the third gear train such that as the sleeve oscillates relative to the housing the at least one gear of the third gear train oscillates along a length of the at least one gear of the first gear train.

4. The assembly of claim 1, wherein the second gear train includes a plurality of gears and a drive wheel eccentrically coupled to one of the plurality of gears.

5. The assembly of claim 4, wherein the drive wheel is received within a recess in the sleeve such that rotation of the drive wheel within the recess causes the sleeve to oscillate relative to the housing.

6. A multi-movement cosmetic assembly, comprising:
a housing defining an interior;
a drive system disposed within the housing;
a sleeve received within the housing; and
a drive shaft positioned in the sleeve;
a motor including a motor shaft;
a drive gear coupled to the motor shaft;
a second gear including a first portion coupled to a first side of the drive gear and a second portion;
a third gear including a first portion coupled to the second portion of the second gear and a second elongated portion;
a fourth gear coupled to the second elongated portion of the third gear; and
a fifth gear coupled to the fourth gear and to the drive shaft
wherein the drive system is operably coupled to the sleeve and the drive shaft such that actuation of the drive system causes (i) the sleeve to move laterally back and forth to oscillate relative to the housing, and (ii) the drive shaft to rotate relative to the housing.

7. The assembly of claim 6, further comprising:
a sixth gear including a first portion coupled to a second side of the drive gear and a second portion; and
a seventh gear including a first portion coupled to the second portion of the sixth gear and a second portion forming a drive wheel configured to engage a recess in the sleeve.

8. The assembly of claim 7, wherein the motor, the drive gear, the second gear, the third gear, the sixth gear, and the seventh gear are provided within the housing, and wherein the third gear and the fourth gear are provided within the sleeve and translate relative to the housing.

9. The assembly of claim 1, wherein the drive shaft is configured to be received by an attachment removably positioned within the sleeve, wherein the attachment includes at least one of a blade and an abrasive member, and wherein the attachment is operably coupled to the drive shaft when the attachment is received in the sleeve such that a rotation of the drive shaft causes a corresponding movement of the at least one of the blade and the abrasive member.

10. A multi-movement cosmetic device, comprising:
a housing defining an interior;
a motor disposed within the housing and including a motor shaft;
a drive gear coupled to the motor shaft;
a first drive train coupled to the drive gear and including an elongated gear;
a second drive train coupled to the drive gear and including a drive wheel; and
a sleeve received within the housing and including:
a drive shaft;
a third drive train coupled to the elongated gear and the drive shaft; and
a recess configured to receive the drive wheel;
wherein actuation of the motor causes (i) the first and third drive trains to rotate the drive shaft; and (ii) the second drive train to rotate the drive wheel within the recess to cause the sleeve to oscillate laterally relative to the housing.

11. The device of claim 10, wherein the first drive train includes a second gear including a first portion coupled to a first side of the drive gear and a second portion, and wherein the elongated gear includes a first portion coupled to the second portion of the second gear and a second elongated portion.

12. The device of claim 11, wherein the second drive train includes:
a fourth gear coupled to the second elongated portion of the elongated gear; and
a fifth gear coupled to the fourth gear and to the drive shaft;
wherein the fourth gear is narrower than the second elongated portion of the elongated gear.

13. The device of claim 10, wherein the third drive train includes:
a sixth gear including a first portion coupled to the drive gear and a second portion;
a seventh gear including a first portion coupled to the second portion of the sixth gear and a second portion forming the drive wheel.

14. The device of claim 10, wherein the drive shaft is configured to be received by an attachment removably positioned within the sleeve, wherein the attachment includes at least one of a blade and an abrasive member, and wherein the attachment is operably coupled to the drive shaft when the attachment is received in the sleeve such that a rotation of the drive shaft causes a corresponding movement of the at least one of the blade and the abrasive member.

15. A multi-movement cosmetic assembly, comprising:
a device including:
a housing defining an interior;
a drive system disposed within the housing; and
a sleeve received within the housing; and
an attachment configured to be removably positioned within the sleeve;
wherein the drive system is operably coupled to the sleeve and the attachment when the attachment is received within the sleeve such that actuation of the drive system causes (i) the sleeve to move laterally back and forth to oscillate relative to the housing, and (ii) the attachment to rotate within the sleeve and relative to the housing; and
wherein the sleeve includes a plurality of circumferentially positioned projections configured to mate with a plurality of circumferentially positioned projections on a hub of the attachment to rotationally fix the hub relative to the sleeve.

16. The assembly of claim 15, wherein the attachment includes a rotatable portion coupled to the hub, and wherein the sleeve includes a support bracket configured to releasably engage the hub to maintain the attachment within the sleeve.

17. The assembly of claim 16, wherein the hub includes an annular groove and the support bracket is received within the annular groove.

18. The assembly of claim 17, wherein the attachment includes a generally cylindrical drum portion rotationally fixed relative to the hub of the attachment.

* * * * *